(12) United States Patent
Hayashi et al.

(10) Patent No.: US 10,046,122 B2
(45) Date of Patent: Aug. 14, 2018

(54) INSUFFLATION SYSTEM

(71) Applicants: FUJIFILM Corporation, Tokyo (JP); OSAKA UNIVERSITY, Osaka (JP)

(72) Inventors: Kentaro Hayashi, Kanagawa (JP); Kiyokazu Nakajima, Osaka (JP)

(73) Assignees: FUJIFILM Corporation, Tokyo (JP); OSAKA UNIVERSITY, Osaka (JP)

( * ) Notice: Subject to any disclaimer, the term of this patent is extended or adjusted under 35 U.S.C. 154(b) by 0 days.

(21) Appl. No.: 14/720,993

(22) Filed: May 26, 2015

(65) Prior Publication Data
US 2015/0250958 A1    Sep. 10, 2015

Related U.S. Application Data

(63) Continuation of application No. PCT/JP2013/081713, filed on Nov. 26, 2013.

(30) Foreign Application Priority Data

Nov. 27, 2012  (JP) .................................. 2012-258654

(51) Int. Cl.
*A61M 13/00*  (2006.01)
*A61M 39/22*  (2006.01)
(Continued)

(52) U.S. Cl.
CPC ....... *A61M 13/003* (2013.01); *A61B 1/00006* (2013.01); *A61B 1/015* (2013.01);
(Continued)

(58) Field of Classification Search
CPC . A61M 13/003; A61M 39/22; A61B 1/00006; A61B 1/015; G02B 23/2476; G02B 23/2469
See application file for complete search history.

(56) References Cited

U.S. PATENT DOCUMENTS 5,246,419 A * 9/1993 Absten ................ A61M 13/003
600/560
2005/0222496 A1   10/2005 Sekiguchi
(Continued)

FOREIGN PATENT DOCUMENTS

CN        1676091       10/2005
JP        62-197029     8/1987
(Continued)

OTHER PUBLICATIONS

"Office Action of China Counterpart Application", dated Mar. 2, 2016, with English translation thereof, p. 1-p. 14, in which the listed foreign reference was cited.
(Continued)

*Primary Examiner* — Lauren P Farrar
(74) *Attorney, Agent, or Firm* — JCIPRNET

(57) ABSTRACT

An insufflation system configured to supply a predetermined gas into a body cavity of a subject includes: an automatic air supply conduit line configured to automatically supply a gas into the body cavity to maintain a predetermined pressure in the body cavity; a manual air supply conduit line configured to supply a gas into the body cavity by a manual operation; a function selection button provided in an endoscope; and a control unit configured to cause, in accordance with an operation of the function selection button, an air supply conduit line selected by an operation of the function selection button to be in a communication state, and cause a non-selected air supply conduit line to be in a disconnection state.

7 Claims, 10 Drawing Sheets

(51) Int. Cl.
- *A61B 1/00* (2006.01)
- *A61B 1/015* (2006.01)
- *G02B 23/24* (2006.01)

(52) U.S. Cl.
CPC ......... *A61M 39/22* (2013.01); *G02B 23/2476* (2013.01); *G02B 23/2469* (2013.01)

(56) References Cited

U.S. PATENT DOCUMENTS

| | | | |
|---|---|---|---|
| 2005/0234391 A1 | 10/2005 | Uesugi et al. | |
| 2006/0004322 A1 | 1/2006 | Uesugi et al. | |
| 2012/0277532 A1* | 11/2012 | Torisawa | A61B 1/015 600/118 |
| 2012/0285460 A1* | 11/2012 | Smith | A61M 16/20 128/205.24 |

FOREIGN PATENT DOCUMENTS

| | | |
|---|---|---|
| JP | 2006-014961 | 1/2006 |
| JP | 2006-130077 | 5/2006 |
| JP | 2012-231897 | 11/2012 |

OTHER PUBLICATIONS

"Search Report of European Counterpart Application", dated Oct. 7, 2015, p. 1-p. 6.

"Written Opinion of the International Searching Authority of PCT/JP2013/081713", this report contains the following items :Form PCT/ISA237(cover sheet), PCT/ISA237(Box No. I),PCT/ISA237(Box No. V), PCT/ISA237(Box No. VI), dated Jan. 14, 2014, which is English translation of "Written Opinion of the International Searching Authority", p. 1-p. 9.

"Office Action of China Counterpart Application" with English translation thereof, dated Oct. 27, 2016, p. 1-p. 13.

"Office Action of China Counterpart Application," with English translation thereof, dated May 9, 2017, p. 1-p. 13.

"Office Action of China Counterpart Application," with English translation thereof, dated Dec. 1, 2017, p. 1-p. 17.

"Office Action of China Counterpart Application," dated Aug. 23, 2017,with English translation thereof, p. 1-p. 13.

"Office Action of Europe Counterpart Application," dated Jun. 7, 2018, pp 1-5.

\* cited by examiner

INSUFFLATION SYSTEM

CROSS-REFERENCE TO RELATED APPLICATIONS

This application is a Continuation of PCT International Application No. PCT/JP2013/081713 filed on Nov. 26, 2013, which claims priority under 35 U.S.C. § 119(a) to Japanese Patent Application No. 2012-258654 filed on Nov. 27, 2012. Each of the above applications is hereby expressly incorporated by reference, in their entirety, into the present application.

BACKGROUND OF THE INVENTION

Field of the Invention

The present invention relates to an insufflation system, and especially relates to an insufflation system that supplies a predetermined gas (for example, carbon dioxide gas) into the body cavity of a subject.

Description of the Related Art

When inspection or treatment is performed using an endoscope, gas is supplied from an air supply conduit line installed in the endoscope into a body cavity in order to secure the visual field of the endoscope and the operation area of a treatment tool. Air is mainly used in the related art as the gas supplied into the body cavity, but a carbon dioxide gas ($CO_2$ gas) is used in recent years. Since the carbon dioxide gas has excellent bio absorbability, damage given to a subject is less. Therefore, the carbon dioxide gas tends to be used as a gas delivery source.

In a case where the carbon dioxide gas is supplied into a body cavity, a gas supply apparatus to which a gas cylinder filled with the carbon dioxide gas is attached is used. The gas supply apparatus is detachably connected with an air supply conduit line of an endoscope, and a carbon dioxide gas from a carbon dioxide gas cylinder is decompressed and supplied.

For example, Japanese Patent Laid-Open No. 2006-014961 (PTL 1) describes an insufflation system that can manually supply a carbon dioxide gas into a body cavity according to operator's operation. In this insufflation system, while there is a merit that it is possible to freely adjust the amount of air supplied into a body cavity according to operator's intention in order to secure the visual field of an endoscope and the operation area of a treatment tool, there is a problem that frequent operation by the operator is required to keep pressure in the body cavity constant and therefore an operation load applied to the operator becomes large.

By contrast with this, Japanese Patent Laid-Open No. 2006-130077 (PTL 2) describes an insufflation system that can automatically supply a carbon dioxide gas into a body cavity such that a predetermined pressure is kept in the body cavity. According to this insufflation system, it is possible to stably control pressure in the body cavity in a desired state without operator's complicated operation, and it is possible to reduce an operation load applied to the operator.

SUMMARY OF THE INVENTION

By the way, in an insufflation system, it is desired to realize an insufflation system having air supply functions of both automatic air supply and manual air supply. According to this insufflation system, it is possible to manually supply a carbon dioxide gas according to operator's operation while automatically supplying the carbon dioxide gas into a body cavity such that pressure in the body cavity becomes a predetermined pressure. Therefore, it is possible to reduce operator's operation load and make fine adjustments to the pressure in the body cavity according to operator's intention, and convenience improves.

However, if manual air supply is performed when the carbon dioxide gas is automatically supplied into the body cavity, air supply becomes excess in the body cavity. That is, when the carbon dioxide gas is supplied by the manual air supply while a predetermined pressure is kept in the body cavity by the automatic air supply, the carbon dioxide gas equal to or greater than the air supply amount intended by the operator is supplied into the body cavity, and the pressure in the body cavity becomes too high. By this means, a load applied to a patient increases. Moreover, since an operation to decrease the pressure in the body cavity by suction means is required in a case where the pressure in the body cavity becomes too high by excess air supply, it is a large load even on the operator.

The present invention is made in view of such circumstances, and it is an object to provide an insufflation system that prevents excess air supply into a body cavity and improves convenience in an insufflation system including air supply functions of both automatic air supply and manual air supply.

To achieve the above-mentioned object, one mode of the present invention is an insufflation system configured to supply a predetermined gas into a body cavity of a subject, including: an automatic air supply conduit line configured to automatically supply a gas into the body cavity to maintain a predetermined pressure in the body cavity; a manual air supply conduit line configured to supply a gas into the body cavity by a manual operation; a selection operation member configured to select any of the automatic air supply conduit line and the manual air supply conduit line; and control means configured to cause an air supply conduit line selected by an operation of the selection operation member to be in a communication state, and cause a non-selected air supply conduit line to be in a disconnection state, in accordance with an operation of the selection operation member.

According to one mode of the present invention, in accordance with the operation of the selection operation member, any one of the automatic air supply conduit line and the manual air supply conduit line is in the communication state and the other is in the disconnection state. Therefore, the automatic air supply conduit line and the manual air supply conduit line are not in the communication state at the same time. Therefore, automatic air supply is not performed when gas is manually supplied into a body cavity, and it is possible to surely prevent excess air supply into the body cavity. As a result, it is possible to separately use the automatic air supply and the manual air supply according to operator's intention without applying a load to a patient, and it is possible to realize an insufflation system with excellent convenience.

The insufflation system according to one mode of the present invention further includes: a first opening-and-closing valve configured to cause the automatic air supply conduit line to communicate and be blocked; and a second opening-and-closing valve configured to cause the manual air supply conduit line to communicate and be blocked, where the control means performs opening-and-closing control of the first opening-and-closing valve and the second opening-and-closing valve, and, out of the first opening-and-closing valve and the second opening-and-closing valve, cause an air supply conduit line selected by the operation of the selection operation member to be in an open state and cause the non-selected air supply conduit line to be in a closed state.

According to this configuration, since an opening-and-closing valve is provided every air supply conduit line, it becomes possible to individually control the communication and block of each air supply conduit line by performing opening-and-closing control of each opening-and-closing valve. Therefore, it is possible to perform exclusive control such that the automatic air supply conduit line and the manual air supply conduit line are in the communication state at the same time. Therefore, automatic air supply is not performed when gas is manually supplied into a body cavity, and it is possible to surely prevent excess air supply into the body cavity.

Moreover, the insufflation system according to one mode of the present invention further includes a direction switching valve configured to selectively switch an air supply conduit line for air supply into the body cavity from the automatic air supply conduit line and the manual air supply conduit line, where the control means performs switching control of the direction switching valve in accordance with the operation of the selection operation member.

According to this configuration, as compared with a case where an opening-and-closing valve is provided every air supply conduit line, it is possible to reduce the number of parts and achieve the simplification of control.

Moreover, the insufflation system according to one mode of the present invention further includes a direction switching valve configured to selectively switch an air supply conduit line for air supply into the body cavity from the automatic air supply conduit line and the manual air supply conduit line, where, when a pressure in the body cavity is equal to or greater than a predetermined pressure, the control means can perform switching control of the direction switching valve.

According to this composition, since it is possible to automatically switch the automatic air supply conduit line and the manual air supply conduit line in a case where the pressure in the body cavity is equal to or greater than the predetermined pressure, it is possible to surely prevent excess air supply into the body cavity.

Moreover, in the insufflation system according to one mode of the present invention, it is preferable that the automatic air supply conduit line and the manual air supply conduit line be connected with the same gas supply source. By sharing the gas supply source in this way, it is possible to achieve the reduction of costs of the entire system.

Moreover, in the insufflation system according to one mode of the present invention, it is preferable that the selection operation member include an operation switch provided in an endoscope. According to this configuration, it is possible to smoothly switch an air supply conduit line for air supply into the body cavity without releasing a hand from the endoscope when the operation of the endoscope is performed.

Moreover, in the insufflation system according to one mode of the present invention, it is preferable that the selection operation member include a foot switch configured to be operated by an operator's foot. According to this configuration, even in a state where both hands are unavailable when the operation of the endoscope is performed, it is possible to smoothly switch an air supply conduit line for air supply into the body cavity without releasing the hands from the endoscope.

According to the present invention, any one of an automatic air supply conduit line and a manual air supply conduit line is in a communication state and the other is in a disconnection state, in synchronization with the operation of a selection operation member. Therefore, the automatic air supply conduit line and the manual air supply conduit line are not in the communication state at the same time. Therefore, automatic air supply is not performed when gas is manually supplied into a body cavity, and it is possible to surely prevent excess air supply into the body cavity. As a result, it is possible to separately use the automatic air supply and the manual air supply according to operator's intention without applying a load to a patient, and it is possible to realize an insufflation system with excellent convenience.

DETAILED DESCRIPTION OF EXEMPLARY EMBODIMENTS

In the following, preferred embodiments of the present invention are described in detail according to the accompanying drawings.

First Embodiment

Figure 1:
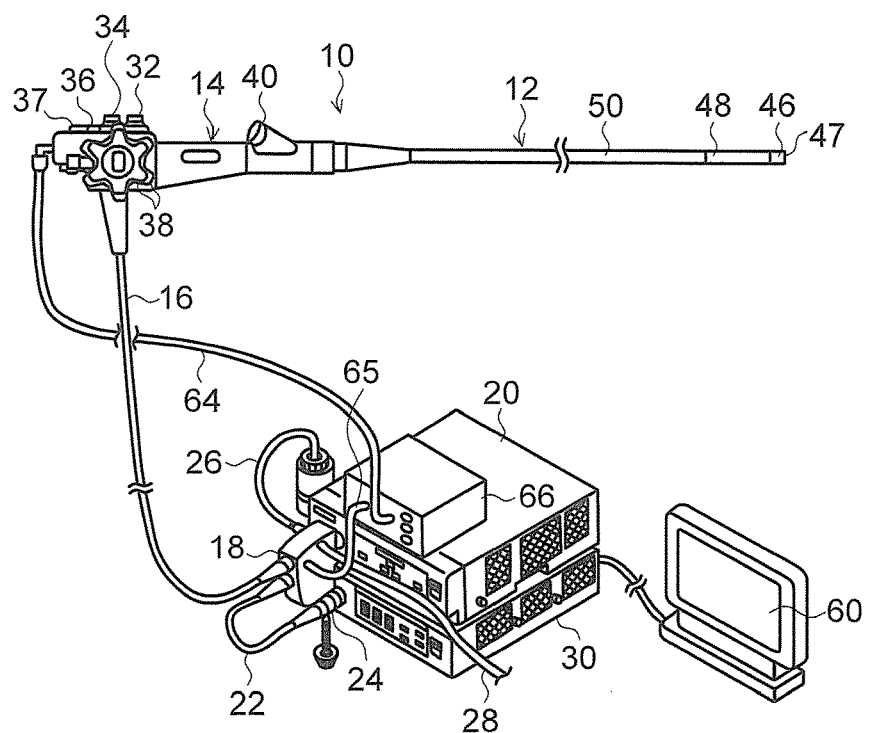
FIG. 1 is an entire configuration diagram indicating a schematic configuration of an endoscope system to which the present invention is applied.

FIG. 1 is a whole configuration diagram illustrating a schematic configuration of an endoscope system to which the present invention is applied. The endoscope system illustrated in FIG. 1 includes an endoscope 10, a light source apparatus 20, a processor 30 and a gas supply apparatus 66.

The endoscope 10 includes an insertion unit 12 inserted in a body cavity and a hand operation unit 14 consecutively connected with this insertion unit 12. A universal cable 16 is connected with the hand operation unit 14, and a LG connector 18 (LG: light guide) is provided in the point of the universal cable 16. By detachably coupling this LG connector 18 with the light source apparatus 20, it is possible to transmit illumination light to an illumination optical system 54 (see FIG. 2) described later. Moreover, an electrical connector 24 is connected with the LG connector 18 through a cable 22, and this electrical connector 24 is detachably coupled with the processor 30. Here, a tube 26 for air supply and water supply and a tube 28 for suction are connected with the LG connector 18.

In the hand operation unit 14, an air supply and water supply button 32, a suction button 34, a shutter button 36 and a function switching button (operation button) 37 are provided in parallel, and a pair of angle knobs 38 and 38 and a forceps insertion unit 40 are provided. Moreover, a gas supply port 44 to supply a carbon dioxide gas into a body cavity is provided in the hand operation unit 14.

Meanwhile, the insertion unit 12 includes a point portion 46, a bend portion 48 and a flexible portion 50, and the bend portion 48 is subjected to bend operation in a remote manner by rotating a pair of angle knobs 38 and 38 provided in the hand operation unit 14. By this means, a point surface 47 of the point portion 46 can be turned toward a desired direction.

Figure 2:
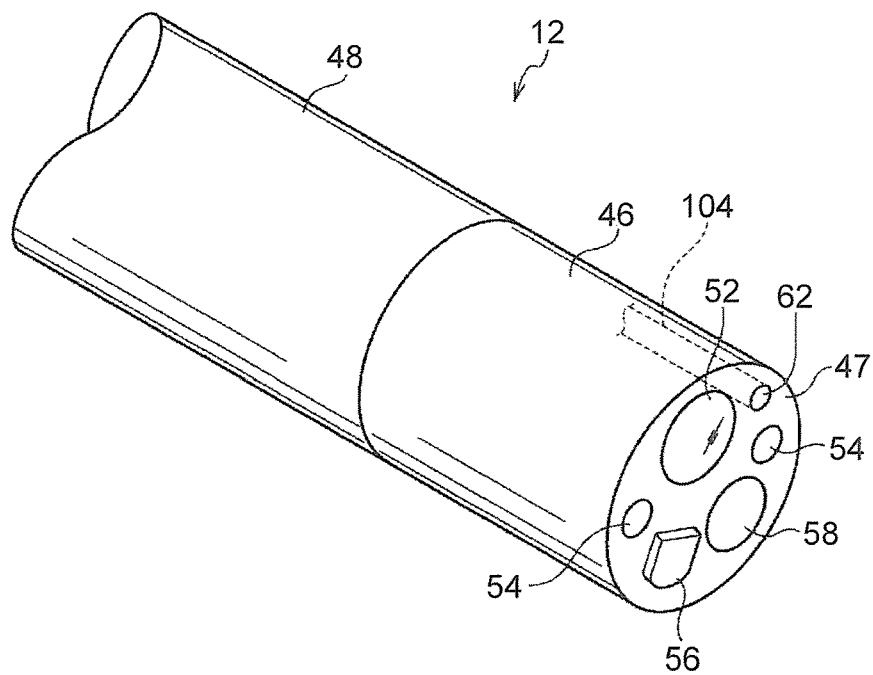
FIG. 2 is a perspective view illustrating a point portion of an insertion unit of an endoscope.

As illustrated in FIG. 2, an observation optical system 52, illumination optical systems 54 and 54, an air supply and water supply nozzle 56 and a forceps port 58 are provided on the point surface 47 of the point portion 46. A CCD (Charge Coupled Device) (not illustrated) is arranged behind the observation optical system 52, and a signal cable is connected with a substrate that supports this CCD. The signal cable is penetrated into the insertion unit 12, the hand operation unit 14 and the universal cable 16 in FIG. 1, extended up to the electrical connector 24 and connected with the processor 30. Therefore, an observation image imported in the observation optical system 52 in FIG. 2 is formed on the light receiving surface of the CCD and converted into an electrical signal, and this electrical signal is output to the processor 30 in FIG. 1 through the signal cable and converted into a video signal. By this means, the observation image is displayed on a monitor 60 connected with the processor 30.

The emitting end of a light guide (not illustrated) is arranged behind the illumination optical systems 54 and 54 in FIG. 2. This light guide is penetrated into the insertion unit 12, the hand operation unit 14 and the universal cable 16 in FIG. 1. Further, the incident end of the light guide is arranged in a light guide stick (see FIG. 3) 19 of the LG connector 18. Therefore, by coupling the light guide stick 19 of the LG connector 18 with the light source apparatus 20, illumination light irradiated from the light source apparatus 20 is transmitted to the illumination optical systems 54 and 54 through the light guide and irradiated from the illumination optical systems 54 and 54.

Figure 3:
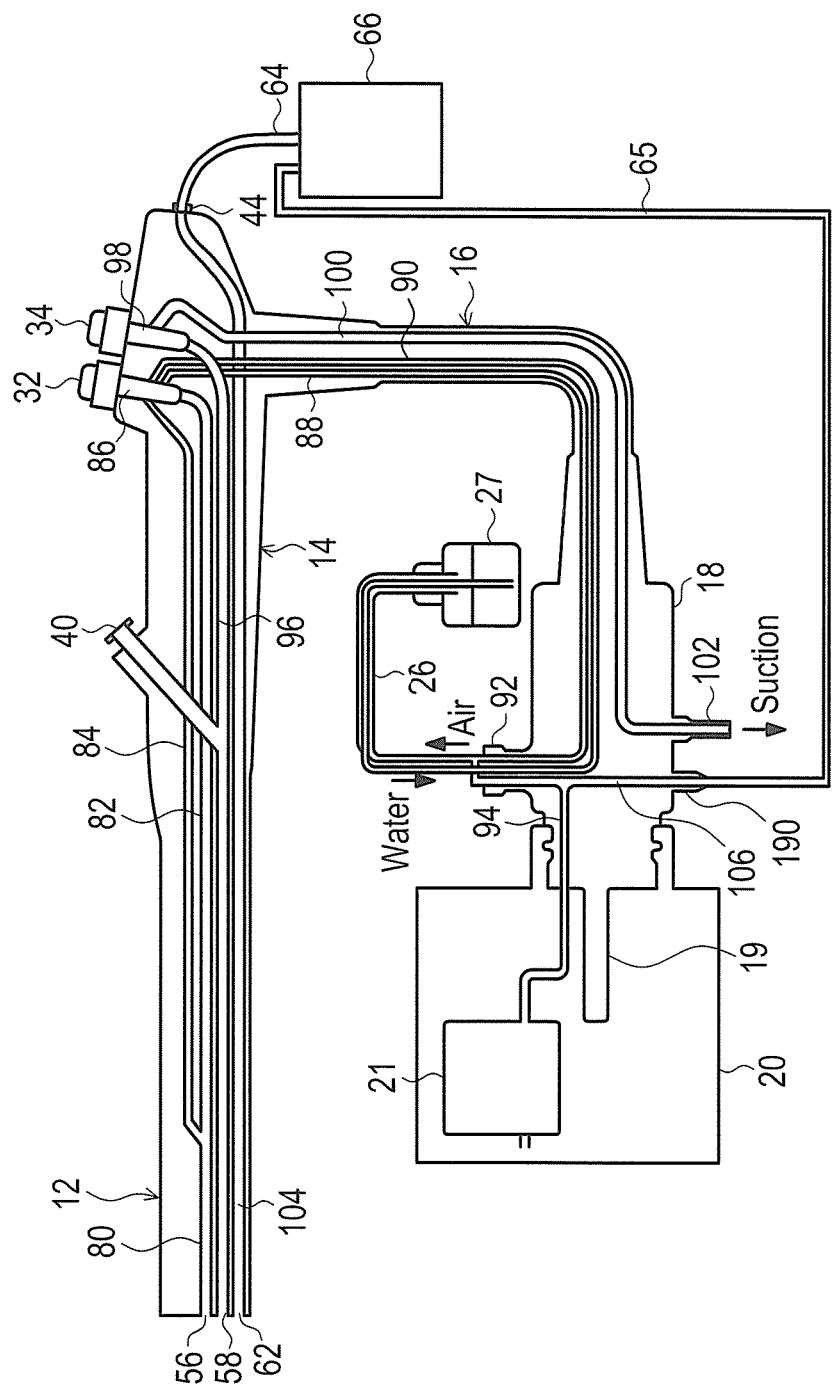
FIG. 3 is a configuration diagram typically illustrating a conduit line configuration of an endoscope.

FIG. 3 is a configuration diagram schematically illustrating a conduit line configuration of the endoscope 10. As illustrated in FIG. 3, an air supply and water supply tube 80 is connected with an air supply and water supply nozzle 56. The air supply and water supply tube 80 diverges into an air supply tube 82 and a water supply tube 84, and each of them is connected with a valve 86 arranged in the hand operation unit 14. An air feeding tube 88 and a water feeding tube 90 are connected with the valve 86, and the air supply and water supply button 32 is attached thereto. The air supply tube 82 and the air feeding tube 88 are communicated in a state where this air supply and water supply button 32 projects, and, by pressing and operating the air supply and water supply button 32, the water supply tube 84 and the water feeding tube 90 are communicated. An air hole (not illustrated) is formed in the air supply and water supply button 32, and the air feeding tube 88 is communicated to the open air through this air hole.

The air feeding tube 88 and the water feeding tube 90 are penetrated into the universal cable 16 and extended up to a water supply connector 92 of the LG connector 18. The tube 26 is detachably connected with the water supply connector 92, and the point of this tube 26 is coupled with a water storage tank 27. Further, the water feeding tube 90 is communicated below the liquid surface of the water storage tank 27, and the air feeding tube 88 is communicated above the liquid surface.

An air tube 94 is connected with the water supply connector 92, and this air tube 94 is communicated to the air feeding tube 88. Moreover, the air tube 94 is communicated to an air pump 21 in the light source apparatus 20 by coupling the LG connector 18 with the light source apparatus 20. Therefore, when the air pump 21 is driven and air is supplied, the air is supplied to the air feeding tube 88 through the air tube 94. This air is assumed to be blown out to the open air through the air hole (not illustrated) when the air supply and water supply button 32 is not operated. Further, when an operator blocks the air hole, air of the air feeding tube 88 is supplied to the air supply tube 82 and air is ejected from the air supply and water supply nozzle 56. Moreover, when the air supply and water supply button 32 is pushed and operated, since the air feeding tube 88 and the air supply tube 82 are blocked, the air fed to the air tube 94 is supplied onto the liquid surface of the water storage tank 27. By this means, the internal pressure of the water storage tank 27 rises and water is supplied to the water feeding tube 90. Further, water is ejected from the air supply and water supply nozzle 56 through the water supply tube 84. Thus, when water or air is ejected from the air supply and water supply nozzle 56 and blown against the observation optical system 52, the observation optical system 52 is cleaned.

Meanwhile, a forceps tube 96 is connected with the forceps port 58. The forceps tube 96 diverges and is communicated to the forceps insertion unit 40 and a valve 98. Therefore, by inserting a treatment tool such as a forceps from the forceps insertion unit 40, it is possible to derive the treatment tool from the forceps port 58. A suction tube 100 is connected with the valve 98, and, in addition, the suction button 34 is attached. The suction tube 100 is communicated to the open air in a state where this suction button 34 projects, and the suction tube 100 and the forceps tube 96 are assumed to be connected by pressing and operating the suction button 34. The suction tube 100 is extended up to a suction connector 102 of the LG connector 18, and it is communicated to an unillustrated suction apparatus by connecting the tube 28 (see FIG. 1) with this suction connector 102. Therefore, it is possible to suck a lesion part, and so on, from the forceps port 58 by pressing and operating the suction button 34 in a state where the suction apparatus is driven.

A gas injection port 62 is formed on the point surface 47 of the point portion 46. A gas tube 104 is connected with the gas injection port 62. The gas tube 104 is connected with the gas supply port 44 arranged in the hand operation unit 14. One end of a gas supply pipe 64 is detachably connected with the gas supply port 44 and the other end of the gas supply pipe 64 is coupled with an automatic air supply connector 144 (see FIG. 4) of the gas supply apparatus 66. By this means, a carbon dioxide gas supplied from the automatic air supply connector 144 of the gas supply apparatus 66 is ejected from the gas injection port 62 through the gas supply pipe 64, the gas supply port 44 and the gas tube 104.

Moreover, a gas connector 190 is provided in the LG connector 18. One end of a gas supply pipe 65 is detachably connected with the gas connector 190 and the other end of the gas supply pipe 65 is coupled with a manual air supply connector 145 (see FIG. 4) of the gas supply apparatus 66. In the LG connector 18, one end of a gas tube 106 is connected with the gas connector 190 and the other end of the gas tube is communicated to the air feeding tube 88 through the air tube 94. By this means, a carbon dioxide gas supplied from the manual air supply connector 145 of the gas supply apparatus 66 is supplied to the air feeding tube 88 through the gas supply pipe 65, the gas connector 190, the gas tube 106 and the air tube 94. Further, similar to a case where air is supplied from the air pump 21 of the light source apparatus 20 to the air feeding tube 88, water or a carbon dioxide gas is ejected from the air supply and water supply nozzle 56 when an operator operates the air supply and water supply button 32.

Here, it is preferable that control means (not illustrated) configured to alternatively control the drive of the carbon dioxide gas supplied from the gas supply apparatus 66 and the air supplied from the air pump 21 be provided such that these gases are not supplied to the air feeding tube 88 at the same time. For example, the control means is provided in the processor 30 and performs control such that the carbon dioxide gas supplied from the gas supply apparatus 66 is provided more preferentially than the air supplied from the air pump 21. In this case, the air pump 21 is used as a preliminary gas supply source in a case where the residual quantity of a carbon dioxide gas cylinder 110 runs out.

Figure 4:
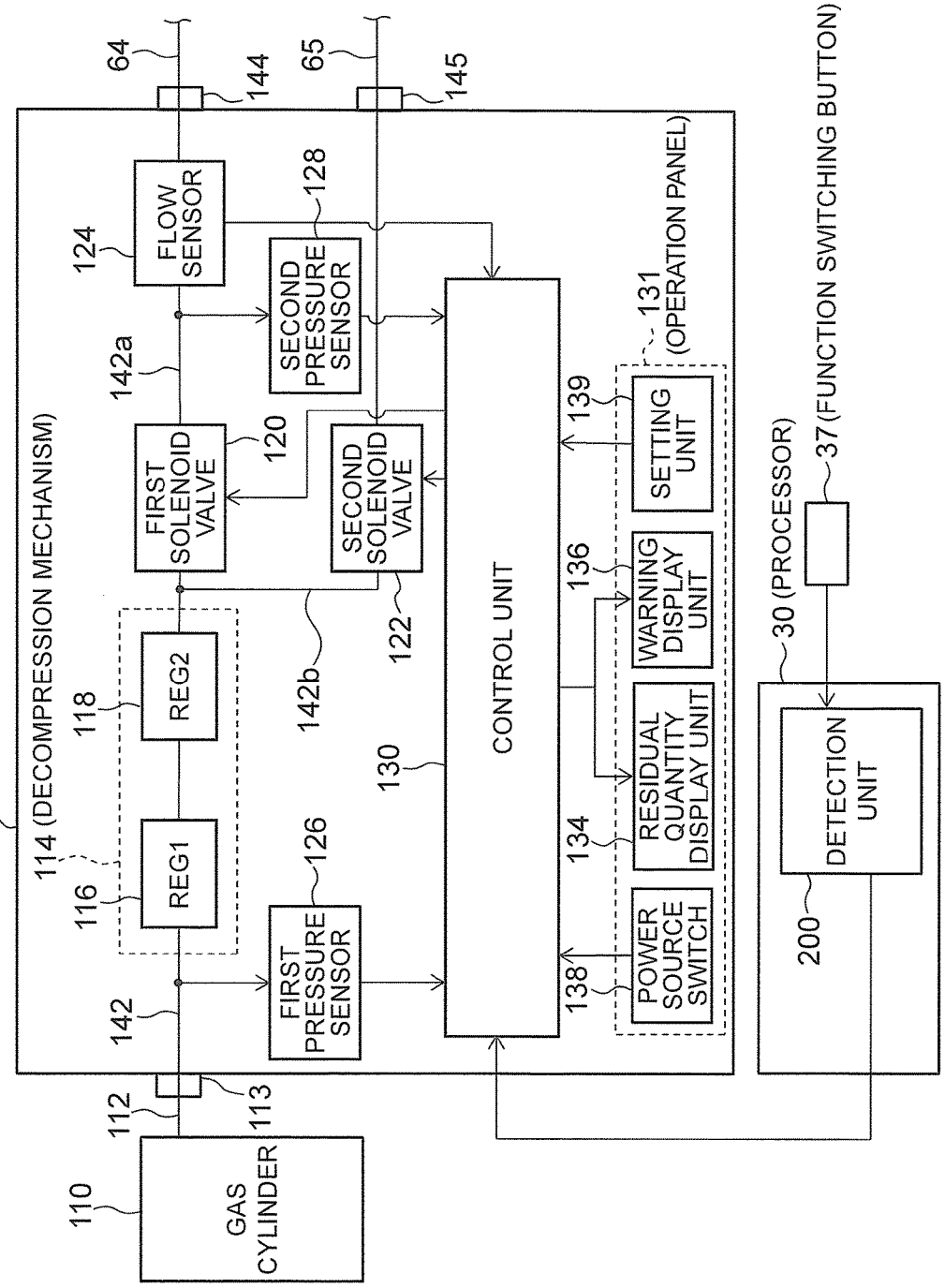
FIG. 4 is a block diagram illustrating a configuration of a gas supply apparatus.

FIG. 4 is a block diagram illustrating the configuration of the gas supply apparatus 66. As illustrated in FIG. 4, the gas supply apparatus 66 includes a decompression mechanism 114, first and second solenoid valves 120 and 122, a flow sensor 124, pressure sensors 126 and 128, a control unit 130 and an operation panel 131.

In a high-pressure connector 113 of the gas supply apparatus 66, one end of a high-pressure hose 112 is detachably coupled with and the other end is connected with the carbon dioxide gas cylinder 110. By this means, it is assumed that a carbon dioxide gas from the carbon dioxide gas cylinder 110 is supplied to the high-pressure connector 113 through the high-pressure hose 112.

One end of an internal conduit line 142 provided in the gas supply apparatus 66 is connected with the high-pressure connector 113. The decompression mechanism 114 to decompress the carbon dioxide gas supplied from the gas cylinder 110 to a predetermined pressure is arranged in the internal conduit line 142, and the outlet side (which is the opposite side to the high-pressure connector 113) of the decompression mechanism 114 diverges into two conduit lines (branch conduit lines) 142a and 142b. One branch conduit line 142a is a conduit line (hereafter referred to as "automatic air supply conduit line 142a") to automatically supply a carbon dioxide gas into a body cavity, and the end part thereof is connected with the automatic air supply connector 144. The other branch conduit line 142b is a conduit line (hereafter referred to as "manual air supply conduit line 142b") to manually supply a carbon dioxide gas into a body cavity, and the end part thereof is connected with the manual air supply connector 145.

The decompression mechanism 114 is formed with two regulators (decompression valves) 116 and 118 disposed in series. The regulators 116 and 118 decompress the pressure of the carbon dioxide gas supplied from the carbon dioxide gas cylinder 110 to a proper pressure in stages. For example, the pressure of the carbon dioxide gas from the carbon dioxide gas cylinder 110 is decompressed from 10 MPa to 0.3 MPa in the first regulator 116. Moreover, the pressure of the carbon dioxide gas decompressed by the first regulator 116 is decompressed from 0.3 MPa to 0.05 MPa in the second regulator 118.

The first solenoid valve 120 is arranged in the automatic air supply conduit line 142a and performs opening-and-closing operation on the basis of a control signal output from the control unit 130. That is, the first solenoid valve 120 functions as the first opening-and-closing valve that enables the automatic air supply conduit line 142a to communicate and be blocked. As the first solenoid valve 120, a flow rate control valve (proportional solenoid valve) that can steplessly control the flow rate in proportion to a control signal (current value) is preferably used. According to a mode in which the first solenoid valve 120 is formed with the flow rate control valve, as compared with a case where an opening-and-closing valve that can only fully open or fully close, it becomes possible to control the flow rate of a carbon dioxide gas supplied into a body cavity at high accuracy.

The second solenoid valve 122 is arranged in the manual air supply conduit line 142b and performs opening-and-closing operation on the basis of a control signal output from the control unit 130. That is, the second solenoid valve 122 functions as the second opening-and-closing valve that enables the manual air supply conduit line 142b to communicate and be blocked. An opening-and-closing valve that can only fully open or fully close is used as the second solenoid valve 122, but, similar to the first solenoid valve 120, a flow control valve may be used.

The flow sensor 124 is arranged between the first solenoid valve 120 and the automatic air supply connector 144 in the automatic air supply conduit line 142a, detects the flow rate (air supply amount) of a carbon dioxide gas supplied into a body cavity through the automatic air supply conduit line 142a and outputs the detection result to the control unit 130.

The first pressure sensor 126 is connected to the internal conduit line 142 between the carbon dioxide gas cylinder 110 and the decompression mechanism 114, detects the pressure of a carbon dioxide gas supplied from the carbon dioxide gas cylinder 110 and outputs the detection result to the control unit 130.

The second pressure sensor 128 is connected between the first solenoid valve 120 and the flow sensor 124 in the automatic air supply conduit line 142a, detects the pressure in a body cavity through a conduit line (the automatic air supply conduit line 142a, the gas supply pipe 64 and the gas tube 104) that communicates into the body cavity, and outputs the detection result to the control unit 130.

A residual quantity display unit 134, a warning display unit 136, a power source switch 138 and a setting unit 139 are provided in the operation panel 131, and each of these units is connected with the control unit 130. An operation button to input a set pressure in the body cavity is provided in the setting unit 139, and, when the set pressure in the body cavity is input by operator's operation, the input signal is output to the control unit 130.

The control unit 130 controls the whole of the gas supply apparatus 66 and is formed including a CPU and a memory (which are not illustrated). A control program to operate the gas supply apparatus 66 and various kinds of setting information (for example, the set pressure in the body cavity, which is input by a setting unit 132) are stored in the memory.

The control unit 130 displays the residual quantity of the carbon dioxide gas of the carbon dioxide gas cylinder 110 on the residual quantity display unit 134, on the basis of the pressure detected in the first the pressure sensor 126. Moreover, when the residual quantity of the carbon dioxide gas becomes equal to or less than a predetermined level, the control unit 130 displays warning by the warning display unit 136 and generates an alai in. By this means, it becomes possible to exchange the carbon dioxide gas cylinder 110 with the new one before the residual quantity of the carbon dioxide gas runs out.

The processor 30 is connected with the gas supply apparatus 66 through a predetermined communication cable. A detection unit 200 that detects the operation of the function switching button 37 of the endoscope 10 is provided in the processor 30. The detection unit 200 outputs a detection signal corresponding to the operation of the function switching button 37 to the control unit 130 of the gas supply apparatus 66.

The control unit 130 performs opening-and-closing control of the first and second solenoid valves 120 and 122 on the basis of the detection signal output from the detection unit 200 of the processor 30.

Figure 5:
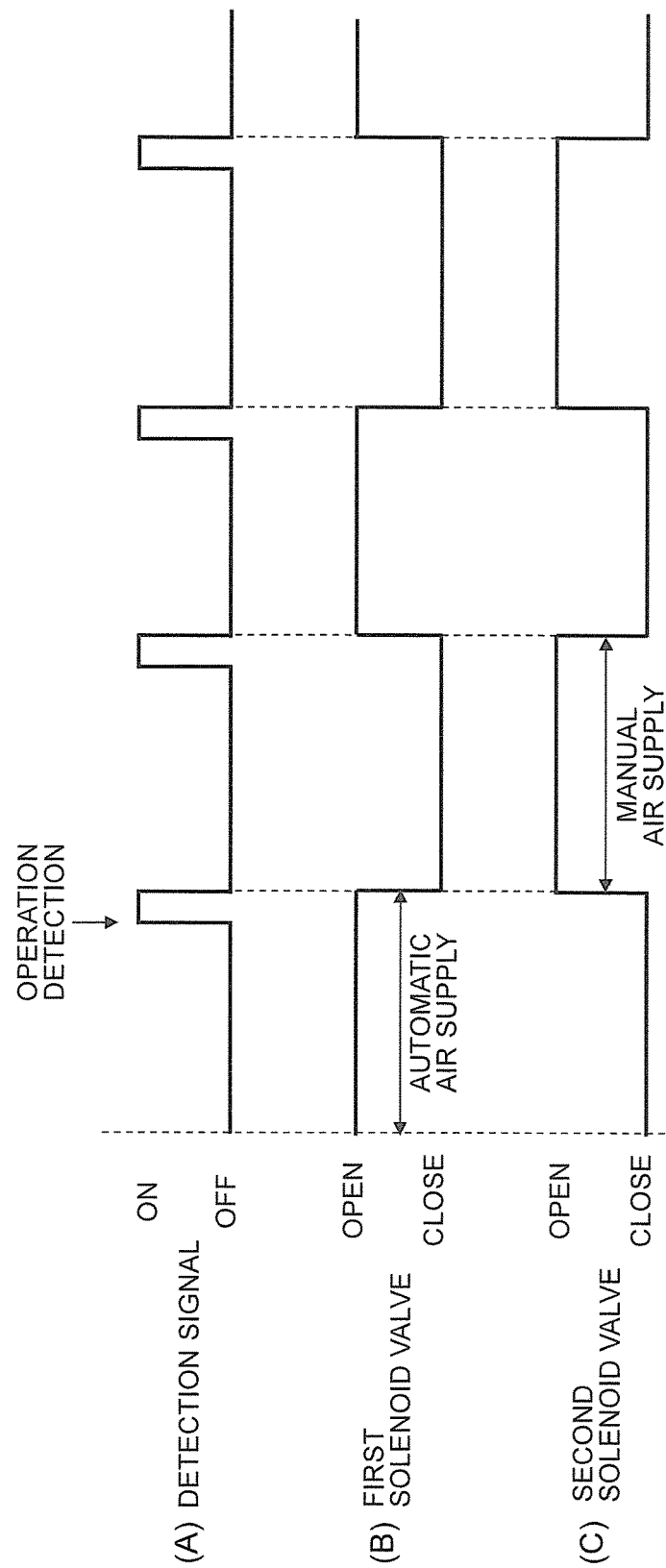
FIG. 5 is a timing chart illustrating a relationship between a detection signal and the opening-and-closing state of each solenoid valve.

FIG. 5 is a timing chart illustrating the relationship between the detection signal output from the detection unit 200 and the opening-and-closing state of the first and second solenoid valves 120 and 122.

As illustrated in part (A) of FIG. 5, the detection signal output from the detection unit 200 is a pulse signal (ON/OFF signal) which is turned on for a certain period of time in a case where the operation of the function switching button 37 of the endoscope 10 is detected and which is turned off in a case where it is not detected.

When the detection signal is turned on, the control unit 130 performs control to switch the open/closed state (opening-and-closing state) of the first and second solenoid valves 120 and 122. At this time, as illustrated in part (B) and part (C) of FIG. 5, exclusive control to make one solenoid valve be in the closed state in a case where the other solenoid valve is in the open state, such that the first solenoid valve 120 and the second solenoid valve 122 are not in an open state at the same time.

Figure 6:
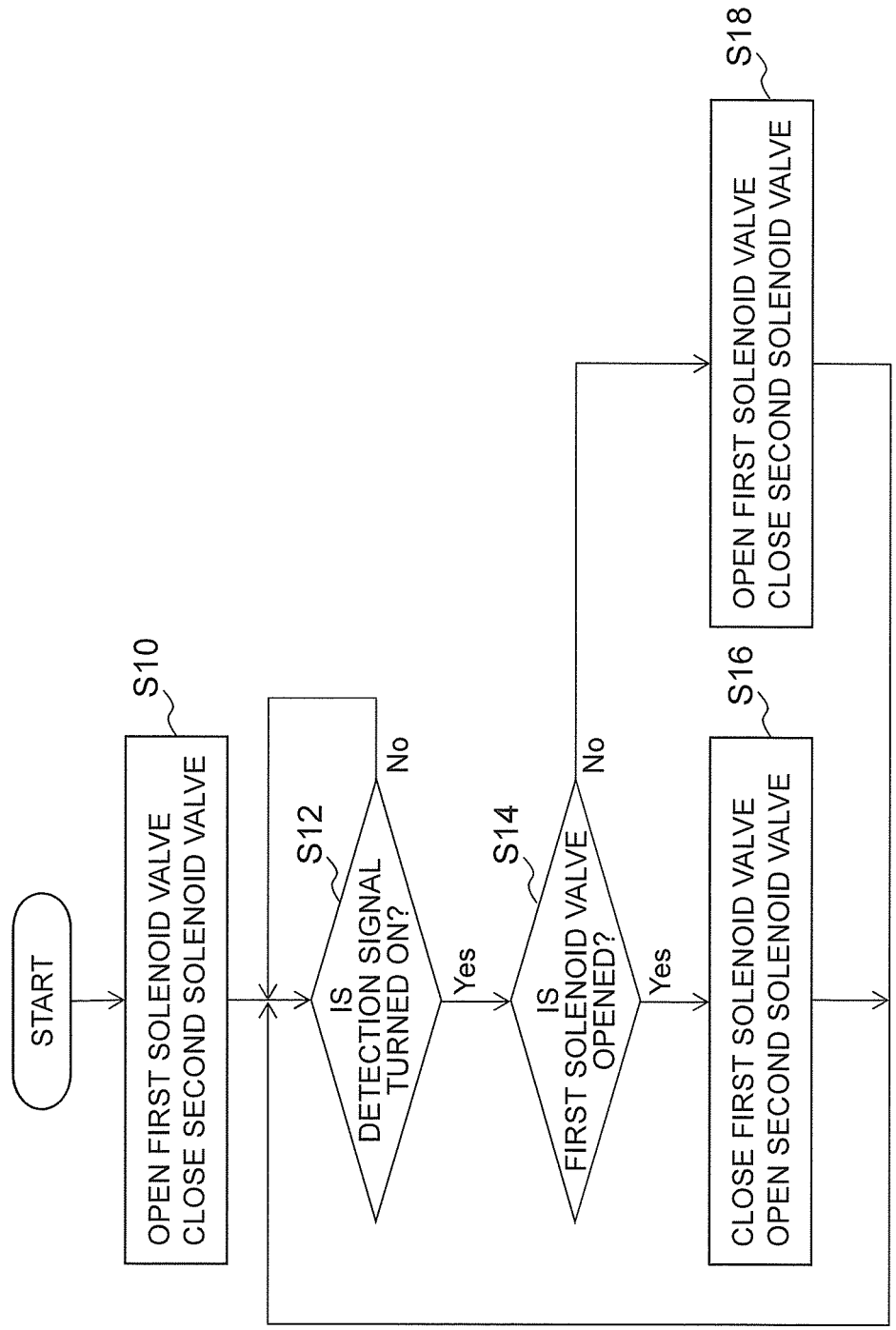
FIG. 6 is a flowchart illustrating one example of a gas supply control method.

FIG. 6 is a flowchart illustrating one example of a gas supply control method performed in the gas supply apparatus 66. Here, it is assumed that the insertion unit 12 of the endoscope 10 is inserted in a body cavity (for example, in a lumen such as a stomach and a large intestine), the power source switch 138 of the gas supply apparatus 66 is turned on and the gas supply apparatus 66 is in an operating state.

First, the control unit 130 makes the first solenoid valve 120 be in an open state, and makes the second solenoid valve 122 be in a closed state (step S10). By this means, the automatic air supply conduit line 142a is in a communication state, and automatic air supply into the body cavity is performed.

That is, after the carbon dioxide gas supplied from the carbon dioxide gas cylinder 110 is decompressed to a proper pressure in stages in the decompression mechanism 114, it is sent to the automatic air supply connector 144 via the automatic air supply conduit line 142a. Further, the carbon dioxide gas sent from the automatic air supply connector 144 is ejected from the gas injection port 62 into the body cavity via the gas supply pipe 64 and the gas tube 104. At this time, the control unit 130 adjusts the carbon dioxide gas supplied into the body cavity to a proper flow rate by performing opening-and-closing control of the first solenoid valve 120 such that the pressure in the body cavity becomes a set pressure, on the basis of the detection results of the second pressure sensor 128 and the flow sensor 124.

Moreover, when automatic air supply into the body cavity is performed, since the manual air supply conduit line 142b is in a disconnection state, a carbon dioxide gas is not sent from the manual air supply connector 145. That is, manual air supply is not performed while the automatic air supply into the body cavity is performed.

Next, the control unit 130 determines whether or not a detection signal output from the detection unit 200 is turned on (step S12).

In a case where the detection signal is not turned on in step S12 (in the case of "No" in step S12), that is, in a case where the operation of the function switching button 37 is not detected, the open/closed states of the first and second solenoid valves 120 and 122 are maintained until the detection signal is turned on.

On the other hand, in a case where the detection signal is turned on in step S12 (in the case of "Yes" in step S12), that is, in a case where the operation of the function switching button 37 is detected, the control unit 130 determines whether or not the first solenoid valve 120 is in an open state (step S14). The open/closed states of the first and second solenoid valves 120 and 122 are stored in the memory, and the control unit 130 can confirm the open/closed states of the first and second solenoid valves 120 and 122 by referring to the memory. Here, instead of the determination processing in step S14, the second solenoid valve 122 may determine whether or not it is in a closed state.

In a case where it is determined in step S14 that the first solenoid valve 120 is in the open state (in the case of "Yes" in step S14), the control unit 130 makes the first solenoid valve 120 be in the closed state and makes the second solenoid valve 122 be in the open state (step S16). By this means, the manual air supply conduit line 142b is in a communication state, and it is in a state where manual air supply into the body cavity is possible.

That is, after the carbon dioxide gas supplied from the carbon dioxide gas cylinder 110 is decompressed to a proper pressure in stages by the decompression mechanism 114, it is sent to the manual air supply connector 145 via the manual air supply conduit line 142b. Further, the carbon dioxide gas sent from the manual air supply connector 145 is ejected from the air supply and water supply nozzle 56 into the body cavity, according to the operation of the air supply and water supply button 32 by the operator.

Moreover, since the automatic air supply conduit line 142a is in a disconnection state when it is in a state where the manual air supply into the body cavity is possible, a carbon dioxide gas is not sent from the automatic air supply connector 144. That is, the automatic air supply is not performed while the manual air supply into the body cavity is performed.

On the other hand, in a case where it is determined in step S14 that the first solenoid valve 120 is not in the open state (in the case of "No" in step S14), the control unit 130 makes the first solenoid valve 120 be in the open state and makes the second solenoid valve 122 be in the closed state (step S18). By this means, similar to the case in step S10, the automatic air supply conduit line 142a is in the communication state, and the automatic air supply into the body cavity is performed. Moreover, the manual air supply conduit line 142b is in a disconnection state, and the manual air supply is not performed while the automatic air supply into the body cavity is performed.

It returns to step S12 after the switching of the open/closed states of the first and second solenoid valves 120 and 122 in step S16 or step S18 is performed in this way, and similar processing is repeatedly executed.

Thus, according to the present embodiment, in synchronization with the operation of the function switching button 37 of the endoscope 10, any one of the automatic air supply conduit line 142a and the manual air supply conduit line 142b is in a communication state and the other is in a disconnection state. Therefore, the automatic air supply conduit line 142a and the manual air supply conduit line 142b are not in the communication state at the same time. Therefore, the automatic air supply is not performed when a carbon dioxide gas is manually supplied into the body cavity, and it is possible to surely prevent excess air supply into the body cavity. By this means, it is possible to separately use the automatic air supply and the manual air supply according to operator's intention without applying a load to a patient, and it is possible to realize an insufflation system with excellent convenience.

Moreover, according to the present embodiment, it is possible to smoothly perform switching between the automatic air supply conduit line 142a and the manual air supply conduit line 142b only by operating the function switching button 37 of the endoscope 10, without releasing a hand from the endoscope 10 when an operator is operating the endoscope 10. Therefore, it is possible to reduce operator's operation load.

Here, a configuration in which the detection unit 200 that detects the operation of the function switching button 37 of the endoscope 10 is provided in the processor 30 has been shown in the present embodiment, but the position in which the detection unit 200 is not especially limited, and it may be provided in other apparatuses (for example, the light source apparatus 20) than the processor 30. Moreover, a configuration in which the detection unit 200 is provided in the gas supply apparatus 66 and directly detects the operation of the function switching button 37 without via other apparatuses.

Moreover, in the present embodiment, a selection operation member is formed with one operation switch (function switching button 37) and air supply conduit lines to supply air into a body cavity are alternately switched every time this operation switch is pushed and operated, but it is not limited to this, and the selection operation member may be formed with multiple operation switches (for example, an operation switch of a push-button type) and an air supply conduit line to supply air into the body cavity may be directly selected. Moreover, the operation switch is not limited to the push-button type, and it may be formed in other types (for example, a slide type and a rotary type, and so on).

Moreover, the present embodiment provides a configuration in which the automatic air supply conduit line 142a and the manual air supply conduit line 142b are connected with the same gas supply source (carbon dioxide gas cylinder 110) as illustrated in FIG. 4, but it is not limited to this, and it may be a configuration in which they are connected with mutually different gas supply sources. However, according to the configuration in which they are connected with the same gas supply source like the present embodiment, it is possible to share the gas supply source and achieve the reduction of costs of the entire system.

Moreover, the present embodiment provides a configuration in which the automatic air supply conduit line 142a and the manual air supply conduit line 142b are selectively switched in synchronization with the operation of the function switching button 37 of the endoscope 10 that is a selection operation member, but it is not limited to this, and, for example, the manual air supply conduit line 142b may be automatically caused to be in a disconnection state in a case where the pressure in a body cavity which is detected by the second pressure sensor 128 is equal to or greater than a predetermined pressure. At this time, the automatic air supply conduit line 142a is in a communication state, but it is possible to surely prevent excess air supply into the body cavity without performing automatic air supply into the body cavity.

Moreover, the present embodiment provides a configuration in which notice is given to an operator by warning display when the residual quantity of a carbon dioxide gas becomes equal to or less than a predetermined level, but it is not limited to this, and, for example, it may make an automatic air supply conduit line in a disconnection state simultaneously with notice to the operator and stop automatic air supply. According to this mode, it is assumed that the consumption of the carbon dioxide gas increases and the residual quantity of a gas cylinder runs out earlier than operator's sense when the manual air supply and automatic air supply are used together in a case where the residual quantity of the carbon dioxide gas decreases, but, by stopping the automatic air supply, it becomes possible to keep the residual quantity of the carbon dioxide gas until the technique is completed.

Second Embodiment

Next, the second embodiment of the present invention is described. In the following, explanation is omitted for common parts with the first embodiment, and characteristic parts of the present embodiment are mainly described.

Figure 7:
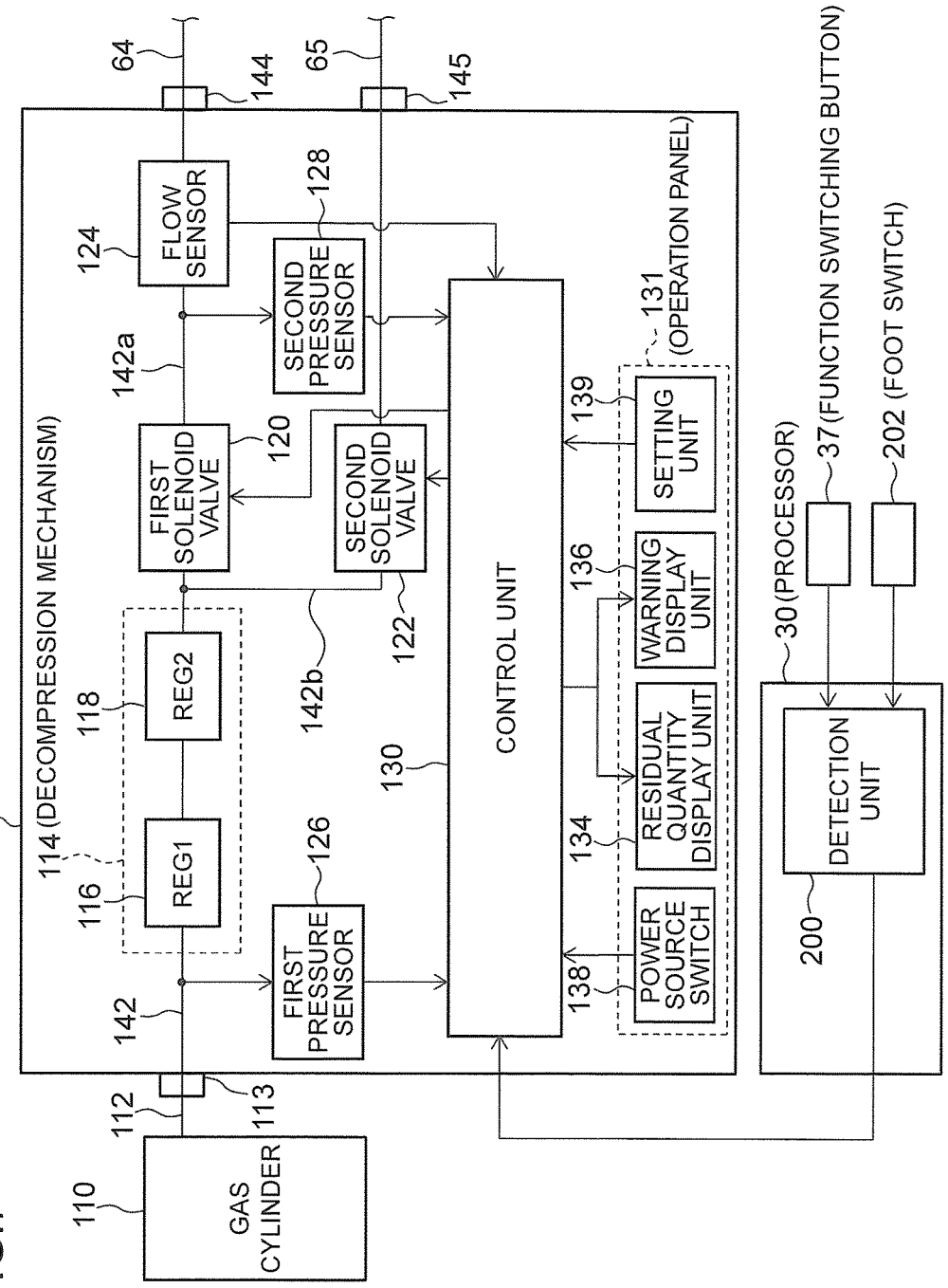
FIG. 7 is a block diagram illustrating a configuration of a gas supply apparatus in the second embodiment.

FIG. 7 is a block diagram illustrating the configuration of the gas supply apparatus 66 in the second embodiment. In FIG. 7, the same reference numerals are assigned to members common with or similar to those in FIG. 4, and explanation thereof is omitted.

As illustrated in FIG. 7, in the second embodiment, when the detection unit 200 of the processor 30 detects the operation of any of the function switching button 37 and a foot switch 202 of the endoscope 10, it outputs a detection signal corresponding to the operation to the control unit 130 of the gas supply apparatus 66. That is, in a case where the detection unit 200 detects the operation of the function switching button 37 or the foot switch 202, it outputs a pulse signal (ON/OFF signal) that turns on it for a certain period of time, and, in a case where it is not detected, it outputs a pulse signal that turns off it. Here, similar to the first embodiment, opening-and-closing control of the first and second solenoid valves 120 and 122 performed in the control unit 130 is performed on the basis of the detection signal output from the detection unit 200.

According to the second embodiment, by operating the foot switch 202 by a foot even in a state where both hands are unavailable when the endoscope 10 is operated, an operator can smoothly perform switching between the automatic air supply conduit line 142a and the manual air supply conduit line 142b without releasing a hand from the endoscope 10. Therefore, as compared with the first embodiment, it is possible to reduce the operation load of the operator.

Third Embodiment

Next, the third embodiment of the present invention is described. In the following, explanation is omitted for common parts with the first embodiment, and characteristic parts of the present embodiment are mainly described.

Figure 8:
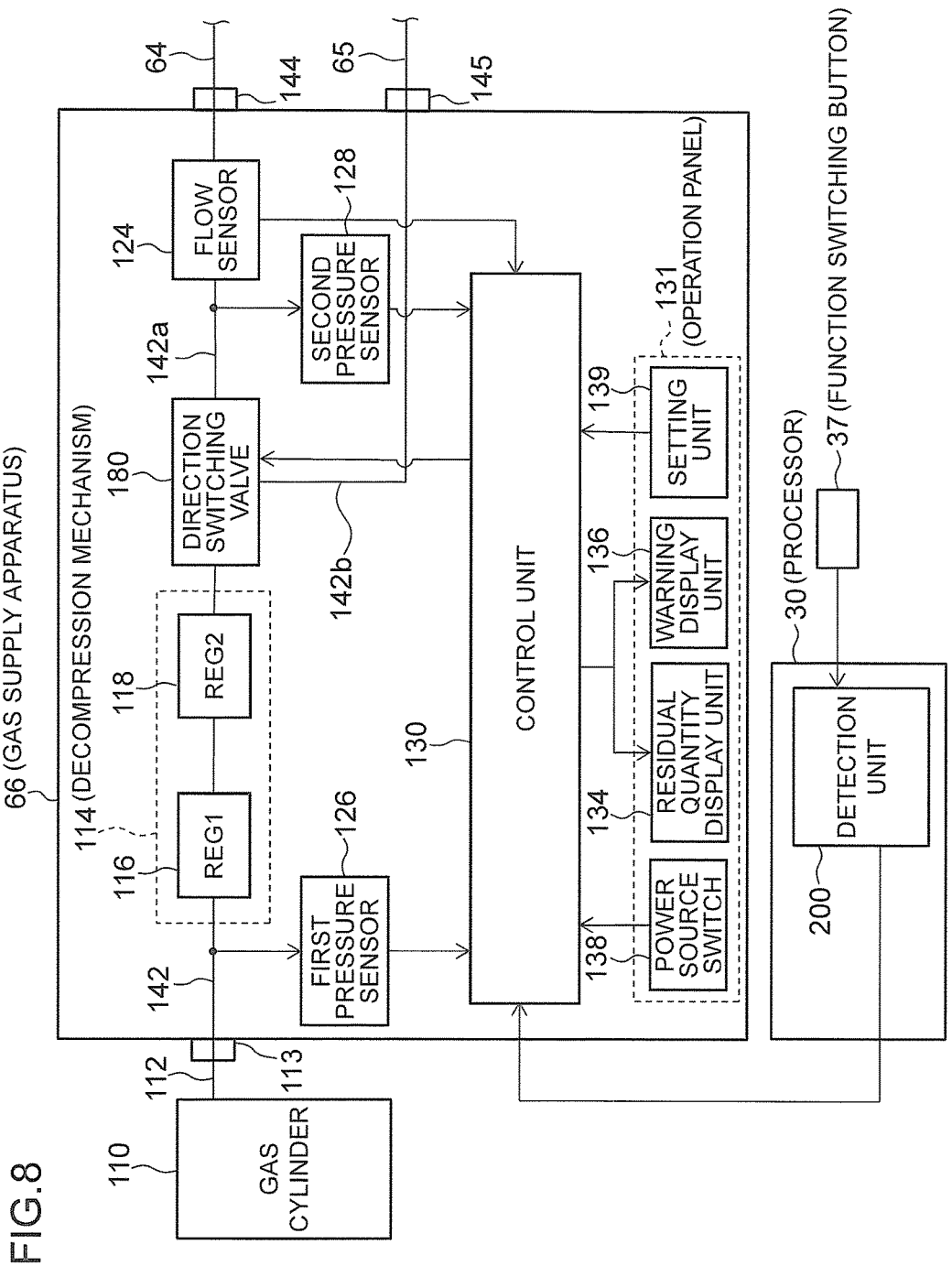
FIG. 8 is a block diagram illustrating a configuration of a gas supply apparatus in the third embodiment.

FIG. 8 is a block diagram illustrating the configuration of the gas supply apparatus 66 in the third embodiment. In FIG. 8, the same reference numerals are assigned to members common with or similar to those in FIG. 4, and explanation thereof is omitted.

In the third embodiment, as illustrated in FIG. 8, a direction switching valve 180 is arranged in the branch unit between the automatic air supply conduit line 142a and the manual air supply conduit line 142b in the outlet side of the decompression mechanism 114 in the internal conduit line 142. The direction switching valve 180 selectively (alternatively) performs switching operation between the automatic air supply conduit line 142a and the manual air supply conduit line 142b which are conduit lines on the outlet side, on the basis of a control signal output from the control unit 130. That is, by the switching operation of the direction switching valve 180, any one of the automatic air supply conduit line 142a and the manual air supply conduit line 142b is in a communication state and the other is in a disconnection state. Here, the switching control of the direction switching valve 180 is basically similar to the first embodiment, and, based on the detection signal output from the detection unit 200 of the processor 30, in a case where the detection signal is turned on (that is, in a case where the operation of the function switching button 37 of the endoscope 10 is detected), the outlet side conduit line of the direction switching valve 180 is selectively switched between the automatic air supply conduit line 142a and the manual air supply conduit line 142b.

Therefore, even in the third embodiment, the automatic air supply conduit line 142a and the manual air supply conduit line 142b are not in the communication state at the same time. By this means, automatic air supply is not performed when a carbon dioxide gas is manually supplied into a body cavity, and it is possible to surely prevent excess air supply into the body cavity. Moreover, as compared with the first embodiment, it is possible to reduce a number of parts and achieve the simplification of control.

Fourth Embodiment

Next, the fourth embodiment of the present invention is described. In the following, explanation is omitted for common parts with the first embodiment, and characteristic parts of the present embodiment are mainly described.

Figure 9:
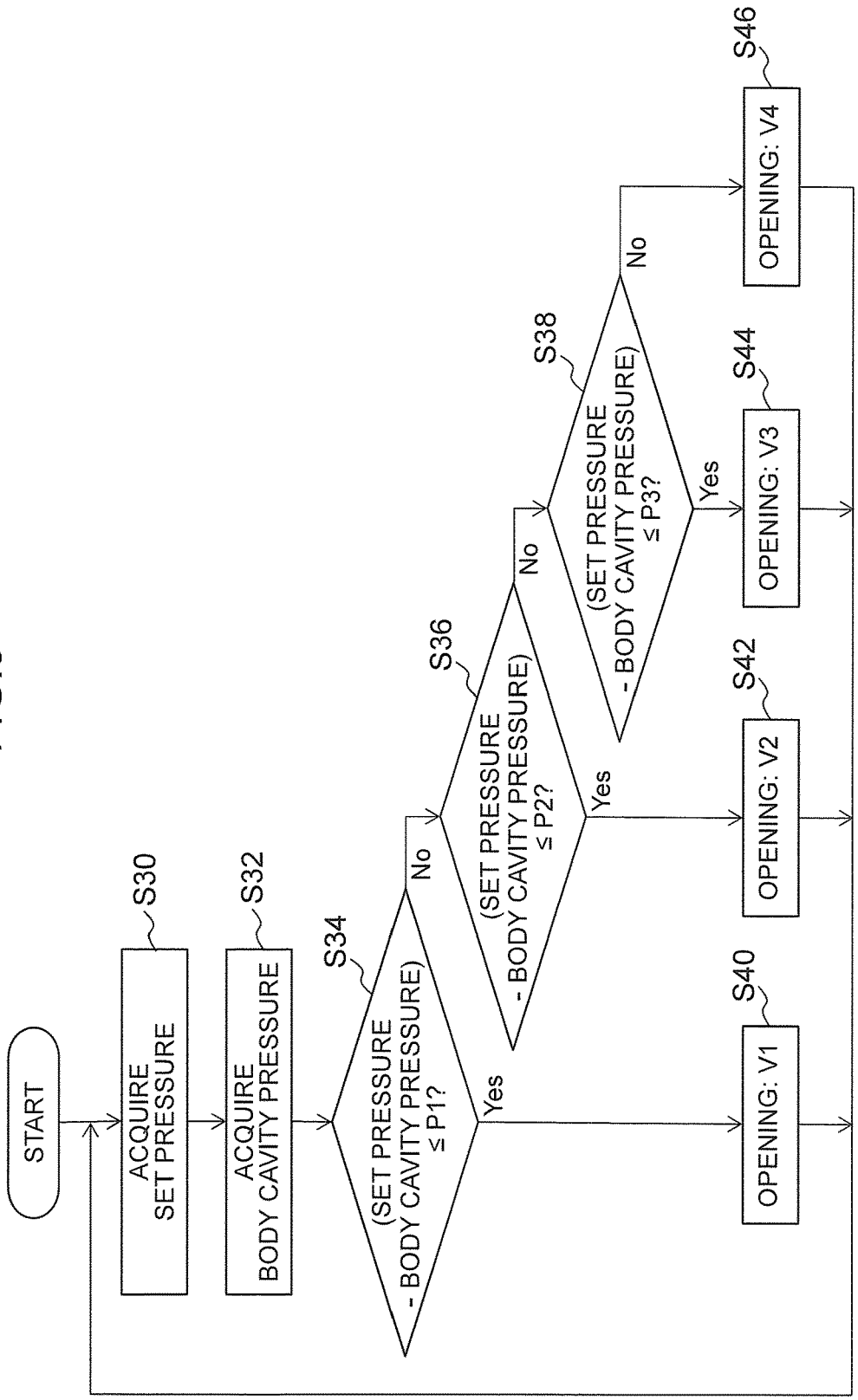
FIG. 9 is a flowchart illustrating one example of an automatic air supply method performed in a gas supply apparatus in the fourth embodiment.

FIG. 9 is a flowchart illustrating one example of an automatic air supply method performed in the gas supply apparatus 66 in the fourth embodiment. Each processing in the flowchart illustrated in FIG. 9 is performed in step S10 or step S18 in FIG. 6. Here, it is assumed that the first solenoid valve 120 is formed with a flow control valve.

First, the control unit 130 acquires the latest set pressure from a memory (step S30) and subsequently acquires pressure in a body cavity (body cavity pressure) detected by the second pressure sensor 128 (step S32).

Next, the control unit 130 changes the opening of the first solenoid valve 120 according to the pressure difference between the set pressure and the body cavity pressure (steps S34 to S46). However, by sequentially comparing the magnitude relationships between first to fourth pressure difference thresholds P1 to P4 (where $0<P1<P2<P3$ is assumed) and the pressure difference between the set pressure and the body cavity pressure, the opening of the first solenoid valve 120 is set within a range of V1 to V4 (where $0<V1<V2<V3<V4$ is assumed).

That is, in a case where the pressure difference between the set pressure and the body cavity pressure is equal to or less than first pressure difference threshold P1 (here, $P1>0$) (in the case of "Yes" in step S34), the control unit 130 assumes the opening of the first solenoid valve 120 as V1 (for example, 25%) (step S40). Here, the first solenoid valve 120 may be made in a closed state (opening 0%) in a case where the body cavity pressure exceeds the set pressure, but, taking into account a carbon dioxide gas absorbed in a living body, it is preferable that the opening of the first solenoid valve 120 be set in an open state within a range that does not exceed V1.

Moreover, in a case where the pressure difference between the set pressure and the body cavity pressure is greater than first pressure difference threshold P1 and equal to or less than second pressure difference threshold P2 (in the case of "Yes" in step S36), the opening of the first solenoid valve 120 is assumed as V2 (for example, 50%) (step S42).

Moreover, in a case where the pressure difference between the set pressure and the body cavity pressure is greater than second pressure difference threshold P2 and equal to or less than third pressure difference threshold P3 (in the case of "Yes" in step S38), the opening of the first solenoid valve 120 is assumed as V3 (for example, 75%) (step S44).

Moreover, in a case where the pressure difference between the set pressure and the body cavity pressure is greater than third pressure difference threshold P3 (in the case of "No" in step S38), the opening of the first solenoid valve 120 is assumed as V4 (for example, 100%) (step S46).

Thus, it returns to step S30 after the opening of the first solenoid valve 120 is set in steps S40 to S46, and similar processing is repeated.

Thus, according to the fourth embodiment, when a carbon dioxide gas is supplied such that the pressure in a body cavity becomes a set pressure, control is performed such that the flow rate (air supply rate) of the carbon dioxide gas gradually decreases as the body cavity pressure becomes closer to the set pressure. That is, while the flow rate increases in a case where the pressure difference between the body cavity pressure and the set pressure is large (for example, immediately after the start of air supply of the carbon dioxide gas, and so on), the flow rate decreases in a case where the pressure difference between the body cavity pressure and the set pressure is small. Therefore, it is possible to suppress a phenomenon that the body cavity pressure varies (changes in an increasing or decreasing manner) around the set pressure, and efficiently set the pressure in the body cavity to the set pressure in a short time.

Here, in the fourth embodiment, the flow path of a carbon dioxide gas is changed by changing the opening of the first solenoid valve 120, but it is not limited to this, and the opening of the first solenoid valve 120 may be kept constant and the opening-and-closing time of the first solenoid valve 120 may be changed, or the flow rate of the carbon dioxide gas may be changed by combining these.

Fifth Embodiment

Next, the fifth embodiment of the present invention is described. In the following, explanation is omitted for common parts with the first embodiment, and characteristic parts of the present embodiment are mainly described.

Figure 10:
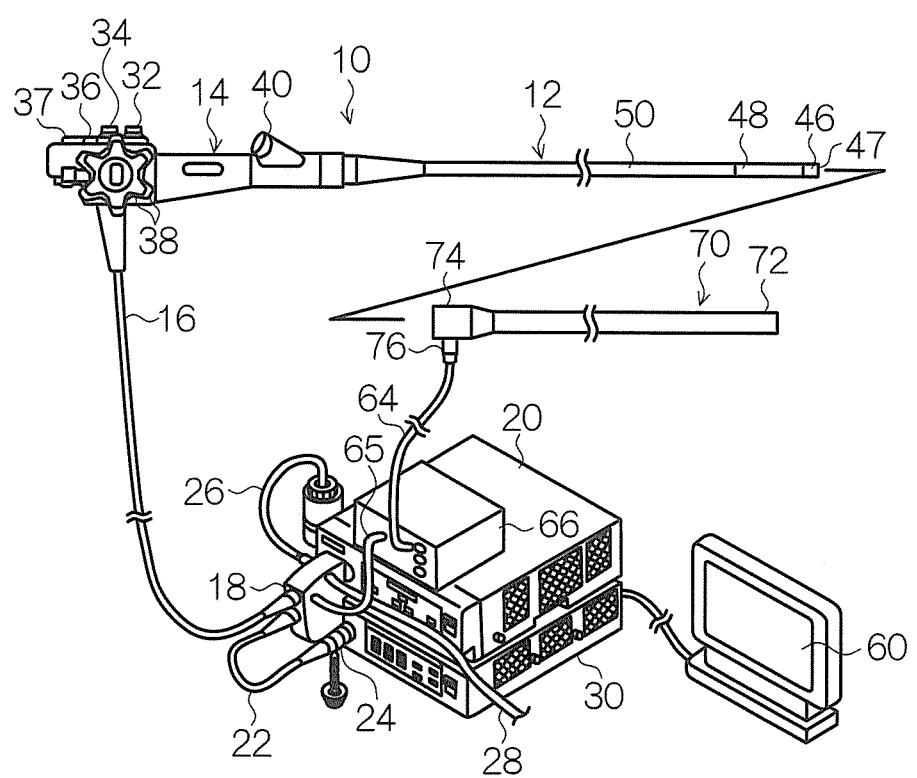
FIG. 10 is an entire configuration diagram illustrating a schematic configuration of an endoscope system in the fifth embodiment.
Figure 11:
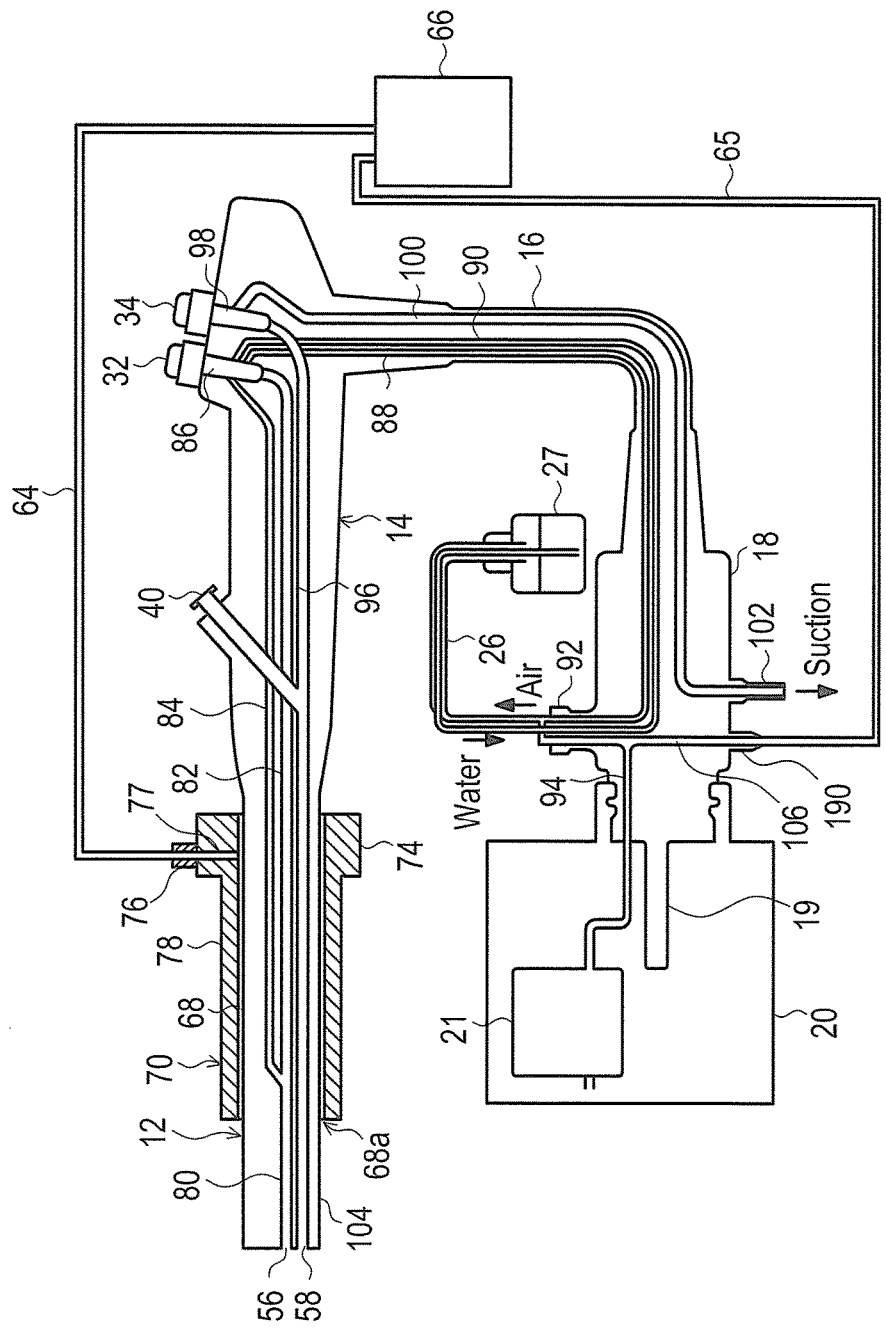
FIG. 11 is a conduit line configuration diagram illustrating an internal configuration of the endoscope illustrated in FIG. 10.

FIG. 10 is a whole configuration diagram illustrating the schematic configuration of an endoscope system in the fifth embodiment. FIG. 11 is a conduit line configuration diagram illustrating the internal configuration of the endoscope illustrated in FIG. 10. In FIGS. 10 and 11, the same reference numerals are assigned to members common with or similar to those in FIGS. 1 and 3, and explanation thereof is omitted.

In the fifth embodiment, as illustrated in FIGS. 10 and 11, the insertion unit 12 of the endoscope 10 is inserted in a body cavity in a state where it is penetrated into an insertion auxiliary tool 70. Further, automatic air supply or manual air supply of a carbon dioxide gas into the body cavity in this state is performed.

The insertion auxiliary tool 70 is formed in a cylindrical shape, has an internal diameter that is slightly larger than the external diameter of the insertion unit 12, and has sufficient flexibility. A hard gripper 74 is provided in the base end of the insertion auxiliary tool 70, and it is assumed that the insertion unit 12 is inserted from this gripper 74.

A gas supply port 76 to supply a carbon dioxide gas is provided on the outer peripheral surface of the gripper 74. One end of a conduit line 77 is connected with the gas supply port 76, and the other end of the conduit line 77 opens against the inner peripheral surface of the insertion auxiliary tool 70 and is communicated to a penetration path 68 formed in the insertion auxiliary tool 70.

One end of the gas supply pipe 64 is detachably connected with the gas supply port 76, and the other end of the gas supply pipe 64 is coupled with the gas supply apparatus 66. By this means, by performing air supply of a carbon dioxide gas from the gas supply apparatus 66, it is supplied from the gas supply port 44 to the penetration path 68 via the conduit line 77, the carbon dioxide gas is introduced from a point opening portion 68a of the penetration path 68, and it is possible to blows up a body cavity with the carbon dioxide gas.

Here, in the penetration path 68 of the insertion auxiliary tool 70, a valve portion member is provided as air tightness means for preventing the outflow of a carbon dioxide gas on the base end side from a position in which the conduit line 77 opens, though illustration is omitted. A slit hole to penetrate the insertion unit 12 is formed in the valve portion member. The shape of the slit hole is not especially limited, but, for example, it is formed in a cross shape. Moreover, from the viewpoint of the maintenance of air tightness, it is preferable that multiple valve portion members be provided in different positions along the axial direction. By this means, it becomes possible to supply a carbon dioxide gas from the point opening portion 68a into a body cavity without causing a carbon dioxide gas supplied from the gas supply apparatus 66 to the penetration path 68 of the insertion auxiliary tool 70 to flow out from the base end side.

According to the fifth embodiment, the penetration path 68 (specifically, a gap formed between the inner wall surface of the penetration path 68 and the insertion unit 12) formed in the insertion auxiliary tool 70 functions as an air supply conduit line to lead the carbon dioxide gas supplied from the gas supply apparatus 66 into a body cavity. Therefore, an air supply conduit line to lead the carbon dioxide gas into the body cavity is unnecessary in the endoscope 10. Therefore, it becomes possible to automatically supply the carbon dioxide gas into the body cavity even in an endoscope that does not include an air supply conduit line for automatic air supply.

Here, a case where a flexible scope such as an upper gastrointestinal endoscopy and a lower gastrointestinal endoscopy is used has been described as one example in each of the above-mentioned embodiments, but the present invention is also applicable to a rigid scope such as a laparoscope.

Moreover, a case where a carbon dioxide gas is supplied into a body cavity has been described as an example, but a gaseous body supplied into the body cavity is not limited to the carbon dioxide gas, and other gases such as a helium gas are possible.

The insufflation system according to the present invention has been described above in detail, but the present invention is not limited to the above-mentioned examples, and it is natural that various kinds of improvement and modification can be performed without departing from the gist of the present invention.

What is claimed is:

1. An insufflation system configured to supply a predetermined gas into a body cavity of a subject, comprising:
   an automatic air supply conduit line configured to automatically supply a gas into the body cavity to maintain a predetermined pressure in the body cavity;
   a manual air supply conduit line configured to supply a gas into the body cavity by a manual operation;
   a selection operation member, wherein the selection operation member is formed with at least one operation switch, the automatic air supply conduit line and the manual air supply conduit line are alternately switched every time when the operation switch is pushed and operated; and
   a control unit configured to perform a control in which gas supply via the automatic air supply conduit and gas supply via the manual air supply conduit are not simultaneously performed, wherein, when the control unit detects operation of the selection operation member while gas supply is performed via one of the automatic air supply conduit and the manual air supply conduit, the control unit causes another one of the automatic air supply conduit and the manual air supply conduit to be in a communication state and causes the one of the automatic air supply conduit and the manual air supply conduit to be in a disconnection state.

2. The insufflation system according to claim 1, further comprising:
   a first opening-and-closing valve configured to cause the automatic air supply conduit line to communicate and be blocked; and
   a second opening-and-closing valve configured to cause the manual air supply conduit line to communicate and be blocked,
   wherein the control unit performs opening-and-closing control of the first opening-and-closing valve and the second opening-and-closing valve, and, out of the first opening-and-closing valve and the second opening-and-closing valve, causes an opening-and-closing valve of the air supply conduit line selected by the operation of the selection operation member to be in an open state and causes the opening-and-closing valve the non-selected air supply conduit line to be in a closed state.

3. The insufflation system according to claim 1, further comprising a direction switching valve configured to selectively switch an air supply conduit line for air supply into the body cavity from the automatic air supply conduit line and the manual air supply conduit line,
   wherein the control unit performs switching control of the direction switching valve in accordance with the operation of the selection operation member.

4. The insufflation system according to claim 1, further comprising a direction switching valve configured to selectively switch an air supply conduit line for air supply into the body cavity from the automatic air supply conduit line and the manual air supply conduit line,
   wherein, when a pressure in the body cavity is equal to or greater than a predetermined pressure, the control unit performs switching control of the direction switching valve.

5. The insufflation system according to claim 1,
wherein the automatic air supply conduit line and the manual air supply conduit line are connected with an identical gas supply source.

6. The insufflation system according to claim 1,
wherein the selection operation member includes an operation switch provided in an endoscope.

7. The insufflation system according to claim 1,
wherein the selection operation member includes a foot switch configured to be operated by an operator's foot.

* * * * *